US00PP26078P3

(12) United States Plant Patent
Egger

(10) Patent No.: US PP26,078 P3
(45) Date of Patent: Nov. 10, 2015

(54) ***SEDUM* PLANT NAMED 'TOUCHDOWN TEAK'**

(50) Latin Name: ***Sedum telephium* (Syn. *Hylotelephium telephium*)**
Varietal Denomination: Touchdown Teak

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 225 days.

(21) Appl. No.: 13/998,100

(22) Filed: Sep. 30, 2013

(65) Prior Publication Data

US 2015/0096091 P1 Apr. 2, 2015

(51) Int. Cl.
*A01H 5/02* (2006.01)

(52) U.S. Cl.
USPC ..... Plt./479
CPC ..... *A01H 5/02* (2013.01)

(58) Field of Classification Search
USPC ..... Plt./479
See application file for complete search history.

(56) References Cited

PUBLICATIONS

Greenhouse Grower. Terra Nova Nurseries Announces New Sedum Touchdown Collection Aug. 15, 2013 retrieved on Jun. 17, 2015, retrieved from the Internet at <http://www.greenhousegrower.com/varieties/terra-nova-nurseries-announces-new-sedum-touchdown-collection/> 5 pp.*

Germania Seed Company. Emerald Coast—Ornamental Grasses and Perennials, retrieved on Jun. 18, 2015, retrieved from the Internet at <https://www.germaniaseed.com/pdf/2014/722_emeraldcoast.pdf> (2013-2014) pp. 1-13.*

* cited by examiner

*Primary Examiner* — June Hwu
(74) *Attorney, Agent, or Firm* — Klarquist Sparkman, LLP

(57) ABSTRACT

A new and distinct hybrid of *Sedum* plant substantially as shown and described, with dark red brown oval leaves, strong, dark red stems, multiple crowns, rose pink flowers, a medium short, upright habit, and excellent vigor.

2 Drawing Sheets

Botanical denomination: *Sedum telephium* (Syn. *Hylotelephium telephium*).

Variety designation: 'Touchdown Teak'.

BACKGROUND OF THE INVENTION

The present invention relates to a new and distinct cultivar of *Sedum telephium* and given the cultivar name of 'Touchdown Teak'. *Sedum* is in the family Crassulaceae. The new cultivar is part of a planned breeding program to make short, compact, multicrown plants. The new cultivar originated from an open pollinated cross with *Sedum* 31-7, a proprietary, unselected seedling, as the seed parent.

Compared to the seed parent, *Sedum* 31-7, the new cultivar, has a much better habit, creamy yellow flowers rather than light pink.

Compared to *Sedum* 'Desert Black', U.S. Plant Pat. No. 24,902, the new cultivar has foliage that is dark red to dark red brown rather than dark brown.

This new and unique *Sedum* is distinguished by:

1. dark red brown oval leaves,
2. strong, dark red stems,
3. multiple crowns,
4. rose pink flowers,
5. a medium short, upright habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the foliage of a 2 year old *Sedum* 'Touchdown Teak' growing in a 2 gallon pot in early spring in Canby, Oreg.

FIG. 2 shows a 2 year old plant of *Sedum* 'Touchdown Teak' in the garden in May in Canby, Oreg.

FIG. 3 shows 2 year old plants in June in the garden in Canby, Oreg.

FIG. 4 shows a close up of the new cultivar in bloom in the trial field in mid September in Canby, Oreg.

DETAILED PLANT DESCRIPTION

The following is a detailed description of the new *Sedum* hybrid based on observations of 18 month old specimens grown in the trial bed in full sun under typical outdoor conditions in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart,* 5th edition.

Plant:
- *Type*.—Herbaceous perennial.
- *Hardiness*.—USDA Zone 4 to 9.
- *Size*.—55 cm tall from the ground to the top the inflorescence and 45 cm wide.
- *Habit*.—Low, clumping upright.
- *Vigor*.—Excellent.

Stem:
- *Number*.—About 9 from base.
- *Size*.—50 cm long and 10 mm wide.
- *Internode length*.—2 cm to 3 cm long.
- *Color*.—Greyed Purple 187A.
- *Texture*.—Succulent.
- *Surface*.—Glabrous.

Leaf:
- *Type*.—Simple.
- *Arrangement*.—Opposite.
- *Shape*.—Oblong.
- *Apex*.—Obtuse.
- *Base*.—Obtuse.
- *Venation*.—Pinnate.
- *Margins*.—Coarsely serrate.
- *Blade size*.—Grows to 6.5 cm long and 3 cm wide.
- *Surface*.—Glabrous on both sides.
- *Texture*.—Thick, spongy, succulent.
- *Petiole*.—Leaves sessile.
- *Leaf color*.—Top and bottom side early spring Brown 200A with base Yellow Green 147A including vein; top and bottom side late spring, early summer between Black 203A and Greyed Purple 187A including vein; top and bottom side summer to fall Greyed Purple 187A including vein.

Inflorescence:
- *Type*.—Terminal, corymbose, umbel-like.
- *Number of flowers*.—About 500 (increases with age).
- *Size*.—Grows to 16.5 cm deep and 13 cm wide.
- *Peduncle*.—50 cm long and 10 mm wide, Greyed Purple 187A, succulent, glabrous. Rachis — grows to 14 cm tall and 5 mm wide, glabrous, Greyed Purple 187A.
- *Pedicels*.—2 mm long, 1 mm wide, glabrous, Greyed Purple N186C.
- *Bloom period*.—August in Canby, Oreg.

Flower bud:
- *Size*.—2.5 mm wide, 4 mm deep.
- *Description*.—Ovoid.
- *Color*.—Greyed Purple 187D with tip Greyed Purple 187A.

Flower:
- *Type*.—Actinomorphic.
- *Shape*.—Stellate.
- *Size*.—4 mm deep and 5 mm wide.
- *Corolla description*.—4 mm deep and 5 mm wide, 5 petals, each lanceolate and 4.5 mm long and 1.5 mm wide, margins entire, tip acuminate, glabrous on both sides, top and bottom side Red Purple 62C on bottom half blending to Greyed Purple 187A at the tip.
- *Calyx description*.—1.3 mm deep and 2 mm wide, stellate, 5 lobes, divided to the base, margins entire, tip acute, glabrous, Greyed Purple N186C.
- *Stamen description*.—10, 3.5 mm long, filaments 3 mm long and Red Purple 62D, anthers Greyed Orange 173C, pollen Yellow Orange 18B.
- *Pistil description*.—2 mm wide and 3 mm deep, Red Purple 61A, with 5 separate prominent carpels, each 3 mm deep and 1 mm wide, Red Purple 61A on top half blending to White N155B on bottom half, style 1.5 mm long, style and stigma Red Purple 61A.
- *Fragrance*.—None.
- *Lastingness*.—Each stem lasts up to a month.

Fruit:
- *Type*.—Ventrally dehiscent follicle, erect, attenuate.
- *Fertility*.—Low.
- *Size*.—2.5 mm wide and 3 mm deep.
- *Color*.—Grey Brown N199B.

Seed: None seen.

Disease and pest resistance or tolerance: Pest and disease resistance are typical for this type of *Sedum*. No known resistances.

I claim:

1. A new and distinct hybrid of *Sedum* plant as herein illustrated and described.

* * * * *

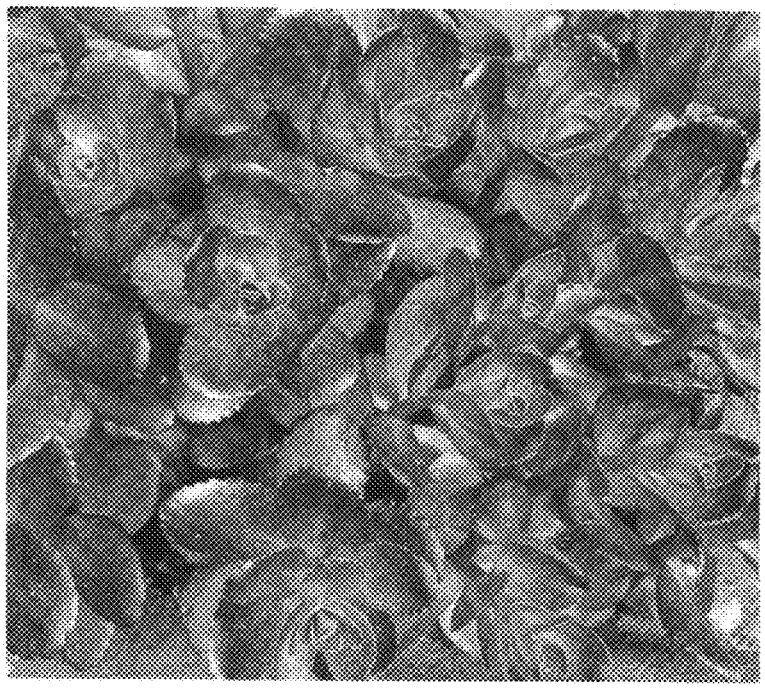
FIG. 1 above, FIG. 2 below
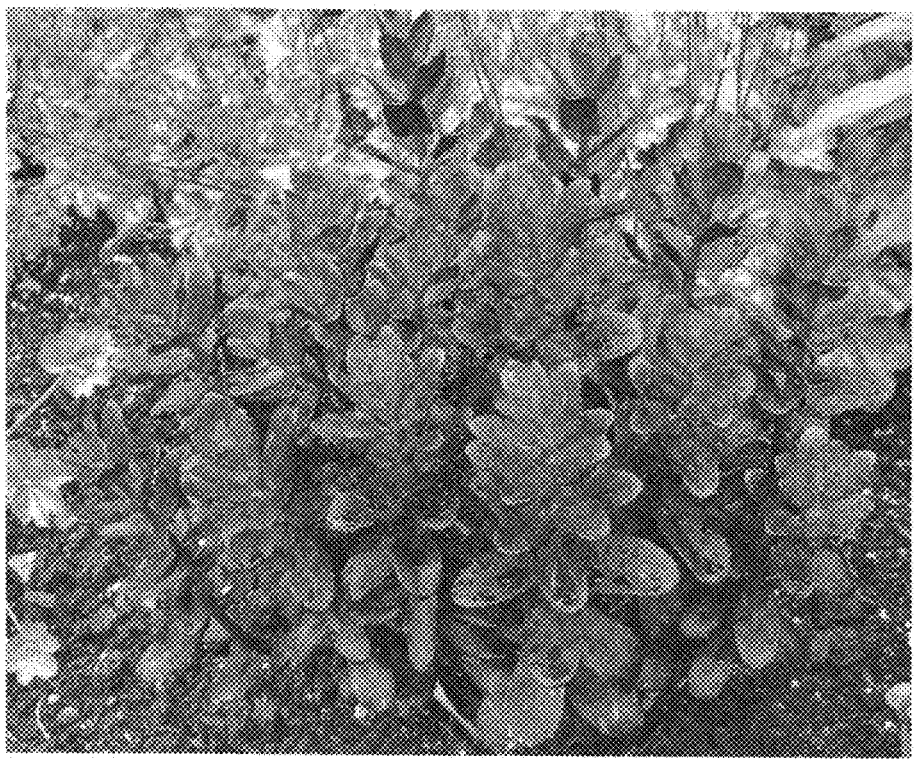

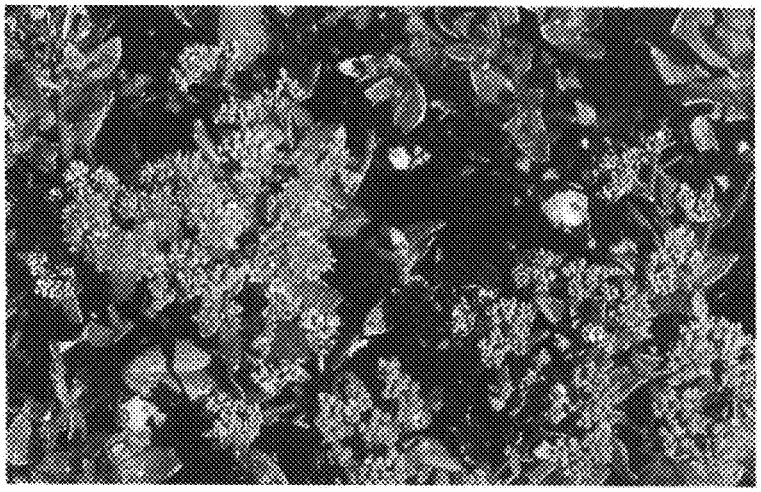

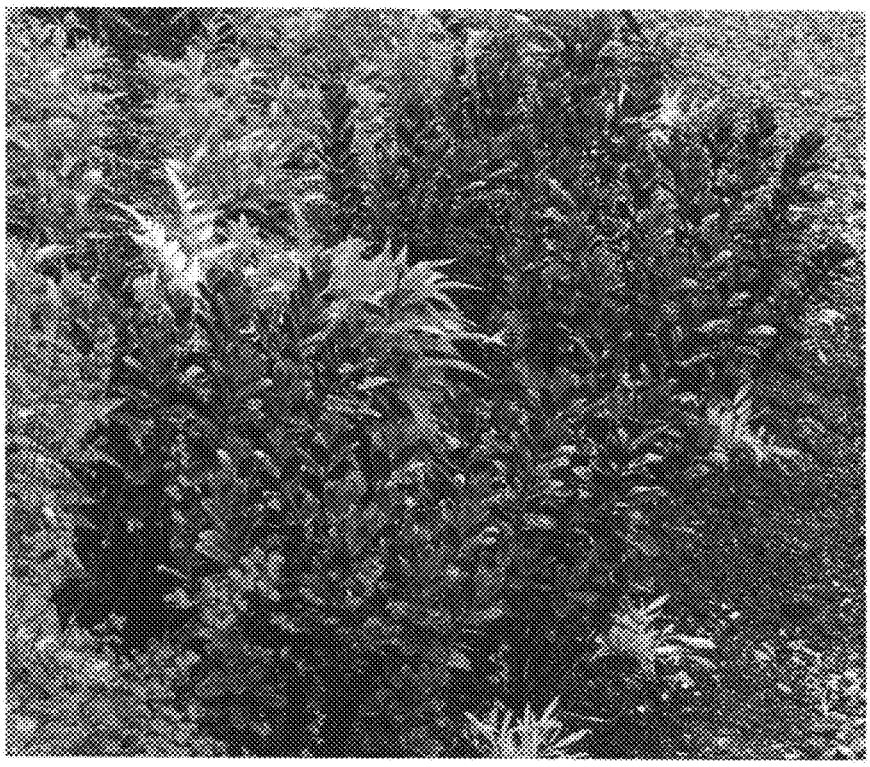
FIG. 3 above, FIG. 4 below